United States Patent [19]

Hutson, Jr. et al.

[11] 4,404,418
[45] Sep. 13, 1983

[54] HF ALKYLATION PROCESS

[75] Inventors: Thomas Hutson, Jr.; Paul D. Hann, both of Bartlesville, Okla.

[73] Assignee: Phillips Petroleum Company, Bartlesville, Okla.

[21] Appl. No.: 385,249

[22] Filed: Jun. 4, 1982

[51] Int. Cl.³ .................................................. C07C 3/54
[52] U.S. Cl. ..................................... 585/710; 585/723
[58] Field of Search ................................. 585/710, 723

[56] References Cited

U.S. PATENT DOCUMENTS

| 2,372,338 | 3/1945 | Penisten | 585/712 |
| 2,417,875 | 3/1947 | Leonard | 585/704 |
| 3,069,483 | 12/1962 | Bauer | 585/723 |
| 3,579,603 | 5/1971 | Jones | 585/719 |
| 3,721,720 | 3/1973 | Chapman et al. | 585/723 |
| 3,993,706 | 11/1976 | Mikulicz et al. | 585/710 |
| 4,041,101 | 8/1977 | Sobel | 585/724 |
| 4,236,036 | 11/1980 | Dixon et al. | 585/723 |
| 4,304,947 | 12/1981 | Hutson | 585/723 |

Primary Examiner—Curtis R. Davis

[57] ABSTRACT

A process for maintaining HF acid soluble oils (ASO) in an HF alkylation reaction zone in an amount sufficient to ensure formation of an alkylate containing a high octane number is provided by returning to the reaction zone a portion of acid soluble oil recovered from an HF catalyst rerun system.

5 Claims, 1 Drawing Figure

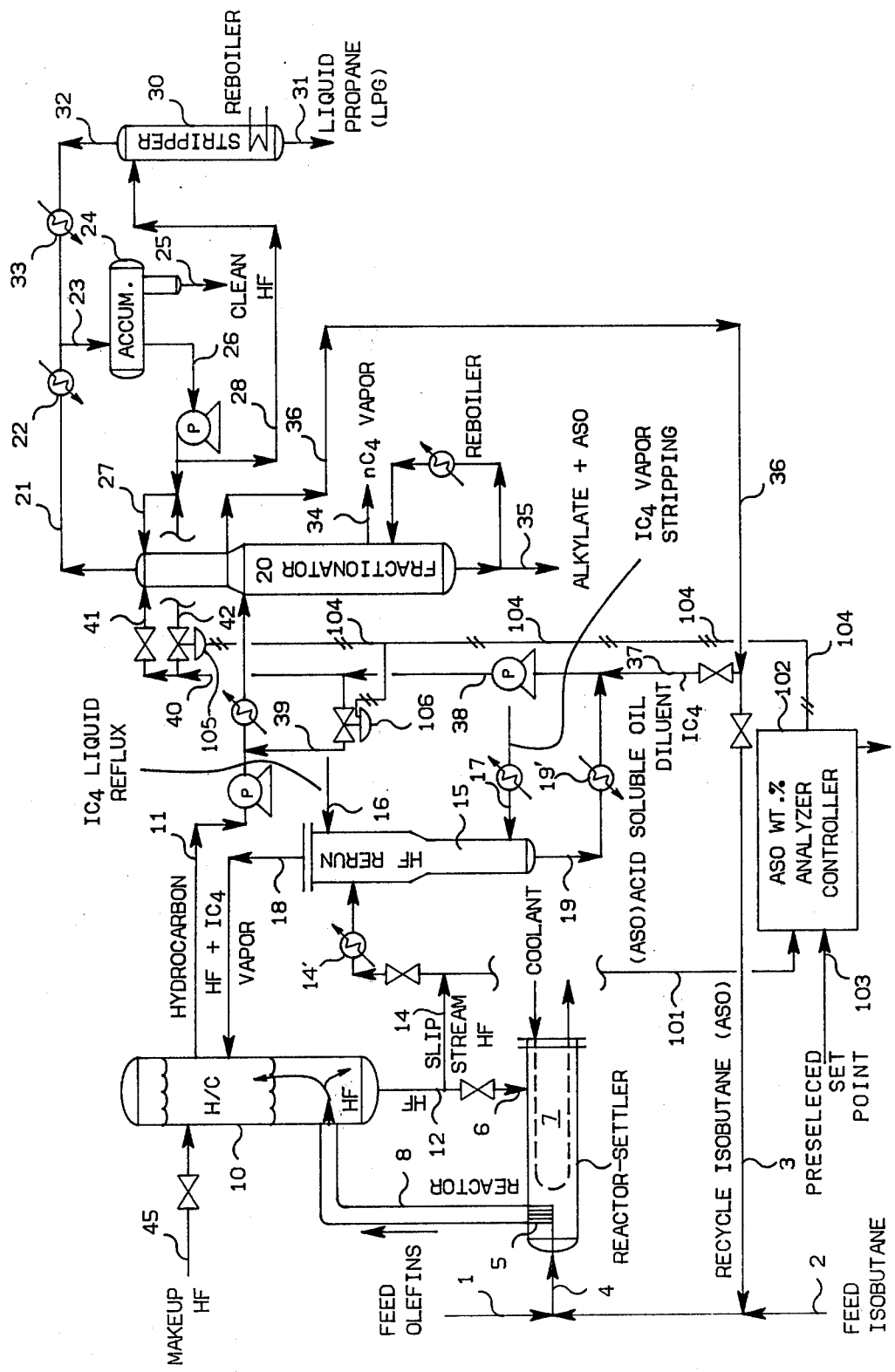

HF ALKYLATION PROCESS

This invention relates to providing a process for maintaining HF acid soluble oils (ASO) in an HF alkylation zone in an amount sufficient to ensure formation of an alkylate product having a high octane number.

Alkylation processes are often employed in the refining industry to produce high octane blending stocks for gasoline. In such processes, it is inevitable that a portion of the feedstock, commonly isobutane and at least one olefin such as butene and propylene react in a manner to form a hydrocarbon having a higher molecular weight than that of the desired alkylate product. At least a portion of this hydrocarbon comprises a viscous polymeric material which is more soluble in HF acid than in hydrocarbon. The resulting viscous liquid component has a higher boiling point than the HF acid component. This higher boiling viscous material is referred to in the industry as HF acid soluble oils, or "ASO".

It is known to those skilled in the art that in the HF alkylation process it is highly desirable to maintain in the HF alkylation reaction zone an amount of ASO sufficient to ensure formation of an alkylate product with a high octane number. This is because it is known that the presence of acid soluble oils in an HF alkylation reaction zone will help ensure the formation of an alkylate with a higher octane number and lesser amounts of high boiling hydrocarbons which are undesired. Therefore, processes which can maintain ASO in an HF alkylation reaction zone in preselected amounts to ensure formation of an alkylate with a high octane number are most advantageous.

Therefore, an object of this invention is to provide a process for maintaining ASO in an HF alkylation zone in the desired amounts to ensure formation of a high quality alkylate.

Other objects, aspects, and advantages of the present invention will become apparent from the following description and accompanying drawing of which shows a schematic flow diagram for carrying out the process of the present invention.

In accordance with the present invention, in an HF alkylation process producing an alkylate and acid soluble oils, an improvement has been discovered which comprises recovering acid soluble oils, diluting the acid soluble oils with liquid isobutane, and returning the acid soluble oils dissolved in liquid isobutane back to the HF alkylation zone in an amount required to ensure production of a quality alkylation product.

The relative amount of acid soluble oil needed to be maintained in an HF alkylation reaction to ensure formation of the desired quality alkylate product, is readily determinable by those skilled in the art according to the quality of alkylate product one desires to obtain. It is recognized by those skilled in the art, however, that the preferred amount of ASO present in an HF alkylation zone constitutes from about 2 to about 5 weight percent based upon the weight of HF acid catalyst present in the HF alkylation zone.

In the process of the present invention, a feedstock such as isobutane and propylene or butene, reacts in the presence of HF catalyst in an HF alkylation reaction zone to produce hydrocarbon product. The reactor effluent is charged to a settler in order to form an upper hydrocarbon liquid phase comprising the alkylate product and a lower HF acid liquid phase comprising ASO dissolved in HF acid. Since it desirable to remove ASO to prevent its buildup, the HF acid catalyst containing ASO is passed to an HF unit rerun column. In this HF rerun column, the HF acid containing ASO is heated, by any means suitable to generate heat, wherein the lower boiling HF is removed overhead as vapor and the higher boiling ASO is separated out and remains in liquid form and is removed as product from the HF rerun column. This acid soluble oil is cooled and then diluted with liquid isobutane recovered from the upper liquid hydrocarbon phase in the settler which was charged to a separation zone. The diluted acid soluble oil in isobutane is then charged to a separation zone where any remaining HF catalyst is driven off. The recovered acid soluble oils dissolved in isobutant are then sent to the HF alkylation reaction zone in an amount required to ensure production of a quality HF alkylation product.

The ASO content of the HF alkylation reaction zone catalyst can be determined by routine laboratory analysis at regular intervals as disclosed in pages 204–206 of *Hydroflouric Acid Alkylation*, 1946, Phillips Petroleum Co. By comparing the actual ASO content of the HF alkylation zone catalyst to the desired predetermined level of ASO in the reaction zone catalyst, the proper amount of ASO diluted with isobutane can then be charged to the separation zone at a locus so that the proper quantity of ASO is recycled in the recycle isobutane stream to the HF alkylation zone so that this desired predetermined level of ASO is maintained in the HF alkylation reaction zone catalyst.

As shown in the drawing, feed olefin stream 1, comprising at least one of propylene, isobutylene, butene-1, cis-butene-2, and trans-butene-2, feed isobutane 2 comprising mainly isobutane with some normal butane, and recycle isobutane 3 comprising isobutane, some normal butane, and subsequently recovery acid soluble oil (AS0) are charged via conduit 4 and nozzles 5 and along with system HF catalyst 6, indirectly cooled in heat exchanger 7 as an emulsion through HF alkylation riser reactor 8 and then to liquid phase separator 10. The separated HF catalyst liquid phase is passed from settler 10 via conduits 12 and 6, and heat exchanger 7 back to riser-reactor 8. Hydrocarbon phase, comprising soluble HF, propane, unreacted isobutane, normal butane, and isopentanes and heavier, the isopentanes and heavier referred to herein as alkylate, is passed via conduit 11 and pump means to reboiled fractionation zone 20, described hereinbelow.

A slip-stream of system HF catalyst, comprising HF, isobutane, and acid soluble oil is passed by valved conduit 14 and indirect heater 14' to HF rerun column 15. Sufficient flow is made via conduit 14 to HF rerun 15 so that the proper amount of ASO can be recovered and returned to the HF alkylation system in the recycled isobutane, further described hereinbelow. HF rerun column 15 is refluxed at 16 with liquid isobutane and stripped with heated vaporized isobutane introduced via conduit 17. Recovered HF and isobutane vapor are returned to the alkylation via conduit 18. Bottoms acid soluble oils from HF rerun column 15 are removed via conduit 19, cooler 19', and are processed as described hereinbelow.

Returning to fractionator 20, the overhead vapor, comprising propane and HF vapor is passed via conduit 21, condenser 22, and conduit 23 to accumulator 24. Two liquid phases are produced in accumulator 24. The lower liquid HF phase is removed via conduit 25 and returned to the HF alkylation. The upper liquid hydrocarbon phase is removed via conduit 26 and is pumped via conduit 27 as reflux for fractionator 20, and by conduit 28 as feed to reboiled stripper 30. Liquid propane is recovered at 31 for sales as LPG (liquefied petroleum gas). Stream 31 can be further treated, as needed, as by solid KOH to remove any remaining HF from the liquid propane. The vaporous overhead from stripper 30 comprises HF and propane and is passed via conduit 32, condenser 33 and conduit 23 to accumulator 24, Condensers 22 and 33 can be a single condenser.

A side stream of normal butane vapor is removed via conduit 34 from fractionator 20. This stream can be condensed and recovered also as liquefied petroleum gas (LPG).

Bottoms stream 35 is recovered from fractionator 20 as alkylate product and has therein the necessary yield of ASO recovered in conduit 19 but not recycled to the alkylation zone in conduit 3.

Liquid isobutane-containing stream is removed from a trap-out tray (not shown) in fractionator 20 via conduit 36 and has therein ASO. Conduit 36 is positioned above feed conduit 11. A portion of stream 36 is passed via conduit 37 as diluent for ASO from conduit 19 and the admixture is pumped in part via conduits 38, 40 and 41 to fractionator 20 at a locus above the feed 11 entry to fractionator 20 via conduit 40 to supply that amount of ASO required (as determined by routine analysis described above) to be recycled in the isobutane returned to the alkylation zone in order to maintain the desired ASO content in the HF system catalyst, e.g. 3.5 weight percent. That amount of ASO required to be removed from the system in the alkylate 35 is passed from conduit 38 via conduit 39 into feed conduit 11. The remainder of the isobutane-containing stream 36, not passed via conduit 37 is recycled via conduit 3 to the alkylation zone. Stream 3 contains that amount of ASO needed to be charged to the alkylation zone to maintain the ASO content in the HF system catalyst at the desired predetermind level.

If desired, a portion of the stream 38 can be charged via conduit 40, conduit 42, and by way of reflux stream 27 to fractionator 20.

In order to maintain the desired preselected weight percent of ASO in the system HF catalyst, a slip stream of system HF catalyst is passed via conduit 101 to ASO weight percent in HF catalyst analyzer 102. Preselected set point 103 is impressed on analyzer 103 and a signal 104 representing the difference between the actual value of ASO in the catalyst and the preselected valve manipulates the flow of ASO in isobutane via stream 38. Valves 105 and 106 are opposite acting. If this difference shows there is less ASO in the system acid than the preselected value, then valve 105 is opened up further (valve 106 is pinched down) and more ASO passes via conduits 40 and 42 so that more ASO is returned to the alkylation plant in recycled isobutane 3. Conversely, if this difference shows there is more ASO in the system acid than the preselected valve, signal 104 causes valve 105 to be further closed (valve 106 being further opened) so that less ASO is returned to the alkylation unit in recycle isobutane stream 3.

Makeup HF can be added to the alkylation zone via conduit 45. The following calculated example further illustrates the process of the present invention:

EXAMPLE

| | | |
|---|---|---|
| (11) | Feed to Fractionator (20), bbls/day | 32,164 |
| (36) | Isobutane, bbls/day | 25,302 |
| (34) | Normal Butane, bbls/day | 425 |
| (31) | Propane, bbls/day | 83 |
| (14) | HF to Rerun (15), bbls/day | 184 |
| | Composition, wt. % | |
| | HF 90 | |
| | iC$_4$ 5 | |
| | ASO 3.5 | |
| | H$_2$O 1.5 | |
| (19) | ASO from Rerun (15), bbls/day | 4 |
| | Composition, wt. % | |
| | HF 0.5 | |
| | iC$_4$ 0.5 | |
| | ASO 98.5 | |
| | H$_2$O 0.5 | |
| (37) | Diluent Isobutane, bbls/day | 16 |
| (40) | Diluent Plus ASO to Fractionator (20), bbls/day | 10* |
| | (Contains 20 wt. % ASO) | |
| (39) | Diluent Plus ASO to Feed (11), bbls/day | 10* |
| (6) | HF in System: | |
| | Composition, wt. % | |
| | HF 90 | |
| | iC$_4$ 5 | |
| | ASO 3.5 (maintained level) | |
| | H$_2$O 1.5 | |
| (35) | Alkylate Yield, bbls/day | 3736 |
| | (Contains 0.107 wt. % ASO) | |

*50-50 Split

In this calculated example, the quantity of ASO produced in alkylation zone 10 is about two barrels per day. This amount of ASO must be removed from the system catalyst in order to maintain the presently desired 2-5 percent weight percent ASO, based on the system HF catalyst.

In order to be sure that sufficient ASO is available to be removed from the system HF catalyst, HF catalyst in the amount of 184 barrels per day in the example is charged via conduit 14 to HF rerun unit 15. This 184 barrels per day of HF catalyst yields about four barrels per day ASO via conduit 19. The ASO, cooled in cooler 19', is diluted with isobutane 36 in conduit 37 so that the mass can be properly pumped, ASO being a highly viscous oil.

Since about two barrels per day of ASO must be removed from the operation so that ASO will not build up to undesired levels in the catalyst in this example, 50 percent of the stream 38 is passed by conduit 39 into the feed stream 11 charging fractionator 20. The ASO in stream 11 is recovered in the bottom product (alkylate) stream 35 and, as is necessary, is removed from the system.

The rest of stream 38, 50 percent in the example, is charged to the fractionator 20 at a locus above the feed 11, as via conduit 40. In fractionator 20, substantially all of the HF is removed from the ASO and the liquid ASO is collected along with liquid isobutane on a trap-out tray from which it is withdrawn via conduit 36, this trap-out tray being above conduit 11 and a portion is recycled via conduit 3 to HF alkylation. The stream 3 contains about two barrels per day of HF ASO, or the excess amount removed in the 184 barrels per day of system acid catalyst charged to HF rerun unit 15, and this two barrels per day must be returned to the HF alkylation to maintain the desired 2-5 weight percent ASO in the system HF catalyst. The ASO added at 40 to fractionator 20 is removed from fractionator 20 in liquid isobutane from a convention trap-out tray.

Stream 3 recycle has the two barrels per day ASO therein.

Reasonable variation and modifications, which will become apparent to those skilled in the art, can be made in this invention without departing from the spirit and scope thereof.

We claim:

1. In an HF alkylation process wherein a preselected amount of acid soluble oils is described to be maintained in the alkylation system HF catalyst the improvement comprises returning a stream comprising acid soluble oils recovered from an HF rerun column and isobutane to the HF alkylation system so as to maintain said preselected amount of acid soluble oils in said system HF catalyst.

2. A process as in claim 1 further comprising measuring the acid soluble oils content in an HF catalyst, comparing that value to the desired preselected content of acid soluble oils in the HF acid catalyst, determining the difference in said acid soluble oils contents, and responsive to the difference returning acid soluble oils dissolved in isobutane back to the HF alkylation zone in an amount sufficient to maintain said preselected amount of acid soluble oils in said system HF catalyst.

3. In an HF alkylation process comprising:
   (a) reacting isobutane and an olefin comprising propylene or butene or a combination thereof in the presence of an HF acid catalyst in an HF alkylation zone to produce a reaction product;
   (b) separating said reaction product in a first separation zone into an upper liquid hydrocarbon phase comprising isobutane and a lower HF catalyst phase comprising acid soluble oils dissolved in HF acid catalyst;
   (c) charging at least a portion of said HF catalyst phase to a HF catalyst rerun zone and recovering therefrom a bottoms fraction from said rerun zone comprising acid soluble oils;
   (d) charging to a second separation zone said upper liquid hydrocarbon phase comprising isobutane and recovering therefrom a stream comprising liquid isobutane; the improvement which comprises:
   (e) diluting said acid soluble oils from step (c) with at least a portion of said liquid isobutane from step (d) to produce diluted acid soluble oils;
   (f) charging at least a portion of said diluted acid soluble oils to said second separation zone at a locus in said separation zone above the removal locus of said liquid of step (d) so as to recover acid soluble oils dissolved in said liquid isobutane; and
   (g) measuring the acid soluble oils content in an HF catalyst, comparing that value to the desired preselected content of acid soluble oils in the HF acid catalyst, and determining the difference in said acid soluble oils contents; and
   (h) responsive to the difference determined in (g) returning acid soluble oils dissolved with liquid isobutane back to the HF alkylation zone in an amount sufficient to maintain a preselected amount of acid soluble oils in the HF acid catalyst to ensure production of quality alkylate product.

4. An HF alkylation process comprising:
   (a) reacting isobutane and an olefin comprising propylene or butene or a combination thereof in the presence of an HF acid catalyst in an HF alkylation zone to produce a reaction product;
   (b) separating said reaction product in a first separation zone into an upper liquid hydrocarbon phase comprising isobutane and a lower HF catalyst phase comprising acid soluble oils dissolved in HF acid catalyst;
   (c) charging at least a portion of said HF catalyst phase to a HF catalyst rerun zone and recovering therefrom a bottoms fraction from said rerun zone comprising acid soluble oils;
   (d) charging to a second separation zone said upper liquid hydrocarbon phase comprising isobutane and recovering therefrom a stream comprising liquid isobutane;
   (e) diluting said acid soluble oils from step (c) with at least a portion of said liquid isobutane from step (d) to produce diluted acid soluble oils;
   (f) charging at least a portion of said diluted acid soluble oils to said second separation zone at a locus in said separation zone above the removal locus of said liquid of step (d) so as to recover acid soluble oils dissolved in said liquid isobutane; and
   (g) measuring the acid soluble oils content in an HF catalyst, comparing that value to the desired preselected content of acid soluble oils in the HF acid catalyst, and determining the difference in said acid soluble oils contents; and
   (h) responsive to the difference determined in (g) returning acid soluble oils dissolved with liquid isobutane back to the HF alkylation zone in an amount sufficient to maintain a preselected amount of acid soluble oils in the HF acid catalyst to ensure production of quality alkylate product.

5. A process as in claim 1, 3, or 4 wherein said acid soluble oils are returned to the alkylation zone in an amount to maintain from about 2 to about 5 weight percent of ASO based on the weight of the HF acid catalyst present in said alkylation reaction zone.

* * * * *